United States Patent [19]

Mezzoli

[11] Patent Number: 5,391,179
[45] Date of Patent: Feb. 21, 1995

[54] NASAL AND/OR RHINOPHARYNGEAL TAMPON

[76] Inventor: Giorgio Mezzoli, Via Ricci Curbastro 56/1, 48022 Lugo (Province of Ravenna, Italy

[21] Appl. No.: 98,090

[22] Filed: Jul. 28, 1993

[30] Foreign Application Priority Data

Sep. 4, 1992 [IT] Italy ............... B092 A 000314

[51] Int. Cl.⁶ ............................. A61M 1/00
[52] U.S. Cl. ........................ 606/196; 604/1
[58] Field of Search .................... 604/1–3, 604/11, 15, 18, 358, 385.1, 904; 606/196, 199

[56] References Cited

U.S. PATENT DOCUMENTS

| | | | |
|---|---|---|---|
| 3,516,407 | 6/1970 | Ruggero | 606/196 |
| 3,850,176 | 11/1974 | Gottschalk | 606/196 |
| 4,030,504 | 6/1977 | Doyle | 606/199 |
| 4,233,025 | 11/1980 | Larson et al. | |
| 4,338,941 | 7/1982 | Bayton. | |
| 4,373,519 | 2/1983 | Errede et al. | 604/367 X |
| 4,568,326 | 2/1986 | Rangaswamy | 606/199 X |
| 4,606,346 | 8/1986 | Berg et al. | 606/196 |
| 4,883,465 | 11/1989 | Brennan | 604/43 X |
| 4,950,280 | 8/1990 | Brennan | 606/196 |
| 5,074,840 | 12/1991 | Yoon | 604/11 X |
| 5,139,510 | 8/1992 | Goldsmith, III et al. | |

FOREIGN PATENT DOCUMENTS 847475 8/1944 Germany .
9222340 12/1992 WIPO ..................... 606/196

*Primary Examiner*—Jerome L. Kruter
*Attorney, Agent, or Firm*—Guido Modiano; Albert Josif; Daniel O'Byrne

[57] ABSTRACT

Nasal and/or rhinopharyngeal tampon including an elongated core, with aspiration holes, around which there is a shaped body made of elastic spongy material covered by a thin deformable membrane made of impermeable material; the core has a stem for connection to an aspiration unit suitable to make the body assume an insertion or extraction configuration having a limited volume in a vacuum state; the flow of air through the stem into the shaped body is suitable to make the body resume an active configuration having a large volume at atmospheric pressure.

5 Claims, 3 Drawing Sheets

NASAL AND/OR RHINOPHARYNGEAL TAMPON

BACKGROUND OF THE INVENTION

The present invention relates to a nasal and/or rhinopharyngeal tampon.

In order to control intranasal and rhinopharyngeal bleeding after surgery, traumas or epistaxis of any kind, it is known to resort to tampons constituted by a long strip of sterile gauze which is forced into the affected cavity after widening the nostril with appropriate divaricators: this is highly traumatic both due to the truly conspicuous amount of material inserted, which often considerably alarms the patient, and due to the unpleasant bleeding which often occurs during the removal of the tampon.

Tampons made of spongy material are also used; these tampons, due to their large volume, are difficult to insert and in any case are unable to effectively compress the upper regions of the nasal septum.

Tampons made of gelatinous material are also used; they become impregnated with blood and slightly increase in volume, but even these tampons are unable to effectively compress the internal structure of the nose, and their removal can often cause bleeding.

As an alternative to these tampons, bags are currently used which are inserted in the nostril in deflated condition and are inflated, and subsequently sealed, in place: these bags, usually made of silicone resins or rubber latex, do not have the drawbacks of gauze tampons but have problems, since they are unable to effectively and uniformly compress the cavity, which has convoluted and nonuniform shape and dimensions, in which they are inserted.

SUMMARY OF THE INVENTION

A principal object of the present invention is to obviate the previously described drawbacks of known devices, i.e. to provide a nasal and/or rhinopharyngeal tampon which is non-traumatic during insertion and removal, effectively compresses in all regions the cavity in which it is inserted and can possibly allow the patient to breathe.

Within the scope of this object, another object of the present invention is to provide a simple structure which is relatively easy to manufacture, safe in use, can be installed quickly, is effective in operation, and has a relatively low cost.

With these and other objects in view, there is provided, according to the present invention, a nasal and/or rhinopharyngeal tampon, which is characterized in that it comprises an elongated core around which there is a shaped body made of elastic spongy material covered by a thin deformable membrane made of impermeable material. The membrane has a stem for connection to an aspiration unit suitable to make the body assume an insertion or extraction configuration having a limited volume, and a flow of air through the stem into the shaped body is suitable to make the body resume an active configuration having a large volume at atmospheric pressure.

BRIEF DESCRIPTION OF THE DRAWINGS

Further features of the present invention will become apparent and evident from the following detailed description of a preferred but not exclusive embodiment thereof, illustrated only by way of non-limitative example in the accompanying drawings, wherein.

DESCRIPTION OF THE PREFERRED EMBODIMENTS

Figures 1A, 1B:
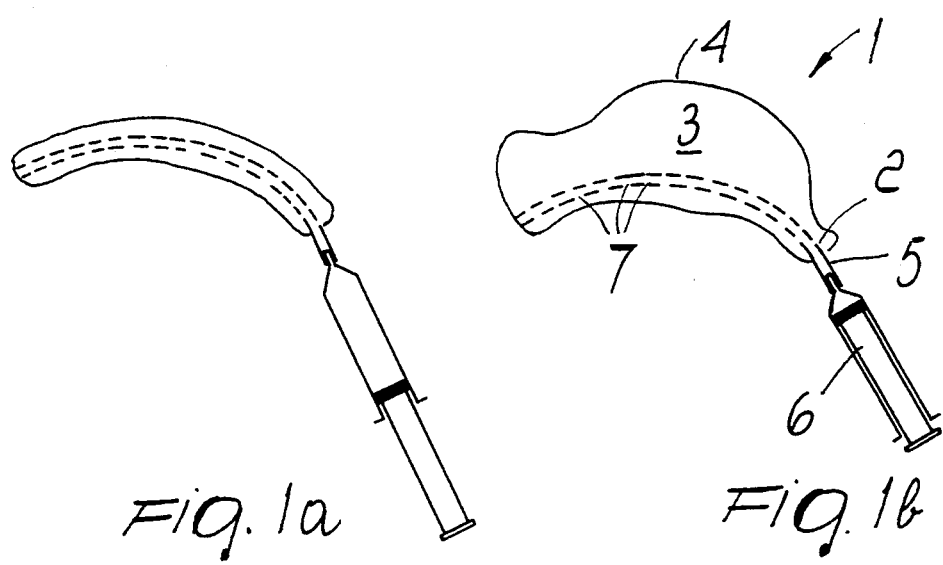
FIGS. 1a and 1b are sectional schematic side views of a nasal and/or rhinopharyngeal tampon according to one aspect of the present invention, respectively in insertion configuration and in active configuration.
Figures 2A, 2B:
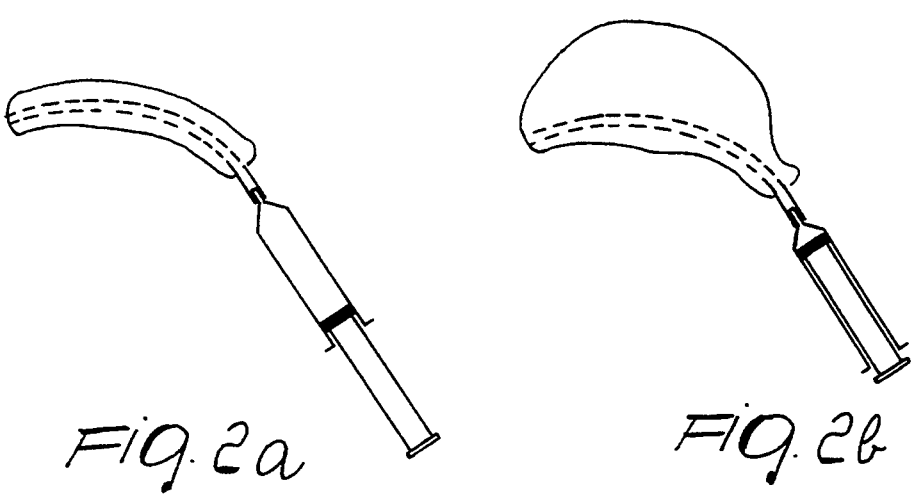
FIGS. 2a and 2b are sectional schematic side views of a nasal and/or rhinopharyngeal tampon according to a further aspect, with variated shape, of the present invention, respectively in insertion configuration and in active configuration.
Figures 3A, 3B:
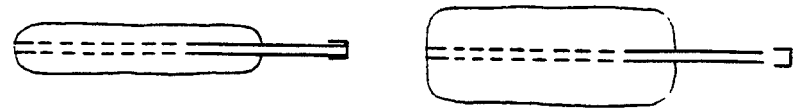
FIGS. 3a and 3b are sectional schematic side views of a nasal and/or rhinopharyngeal tampon according to a further aspect, with variated shape, of the present invention, respectively in insertion configuration and in active configuration.
Figures 4A, 4B:
FIGS. 4a and 4b are sectional schematic side views of a nasal and/or rhinopharyngeal tampon according to a further aspect, with variated shape, of the present invention, respectively in insertion configuration and in active configuration.
Figure 5A:
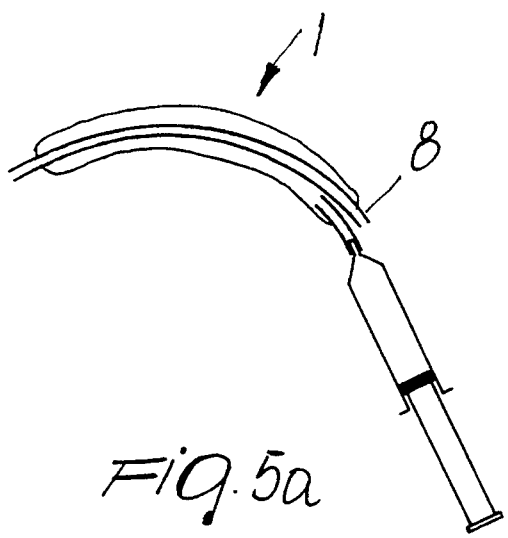
FIGS. 5a and 5b, 6a and 6b, 7a and 7b, and 8a and 8b are views similar to the preceding ones according to a further aspect of the present invention, in which a breathing tube is provided.
Figure 5B:
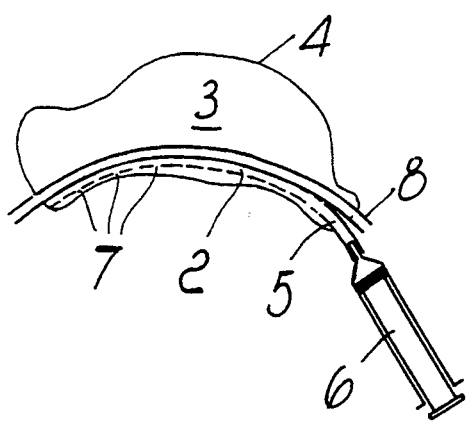
Figure 6A:
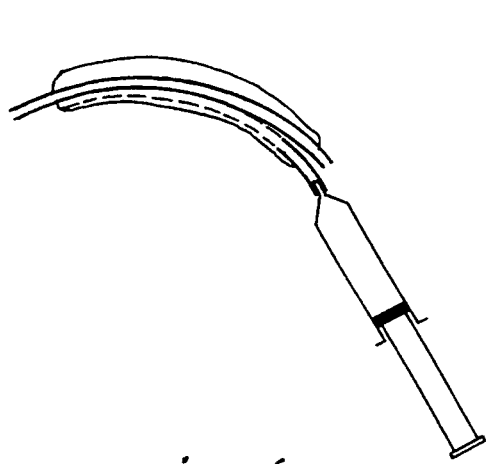
Figure 6B:
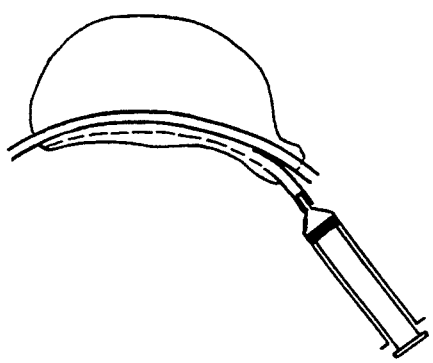
Figure 7A:
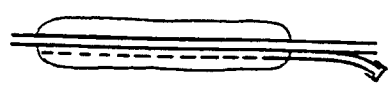
Figure 7B:
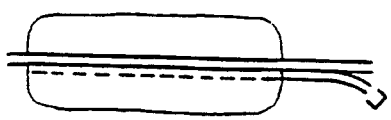
Figure 8A:
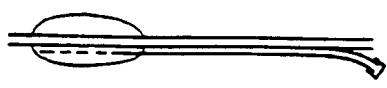
Figure 8B:
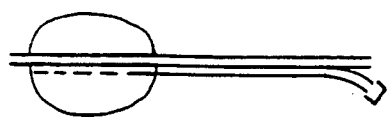
Figure 9A:
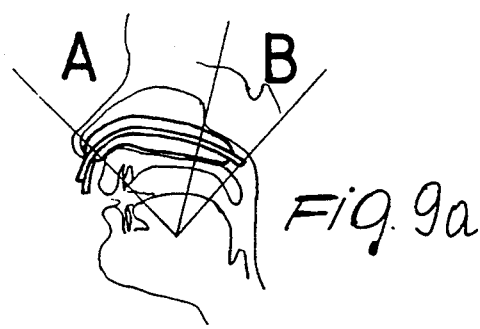
FIGS. 9a and 9b are schematic sectional side views of the tampon from figures 1a and 1b inserted in the nasal and rhinopharyngeal cavities, respectively in insertion configuration and in active configuration.
Figure 9B:
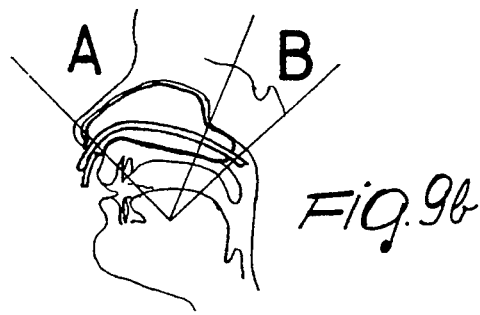
Figure 10A:
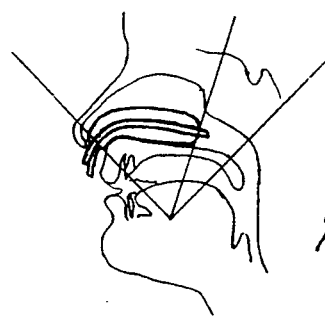
FIGS. 10a and 10b are schematic sectional side views of the tampon from FIGS. 2a and 2b inserted in the nasal cavity, respectively in insertion configuration and in active configuration.
Figure 10B:
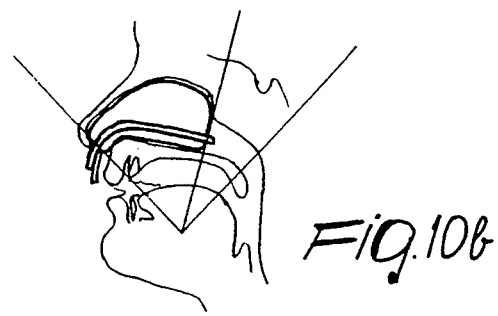
Figure 11A:
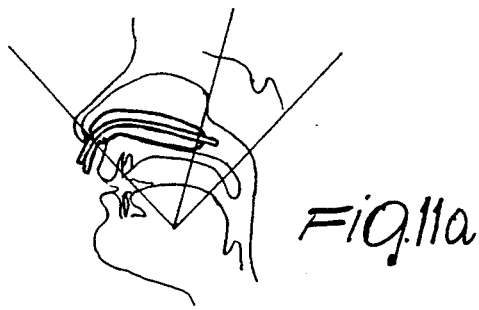
FIGS. 11a and 11b are schematic sectional side views of the tampon from FIGS. 3a and 3b inserted in the nasal and rhinopharyngeal cavities, respectively in insertion configuration and in active configuration.
Figure 11B:
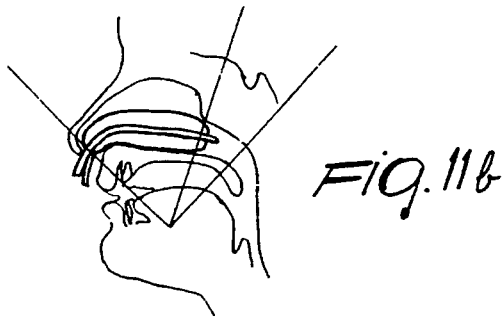
Figure 12A:
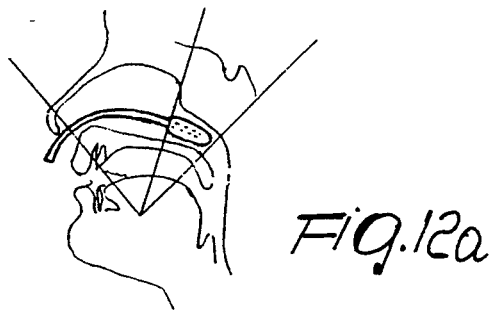
FIGS. 12a and 12b are schematic sectional side views of the tampon from FIGS. 4a and 4b inserted in the rhinopharyngeal cavity, respectively in insertion configuration and in active configuration.
Figure 12B:
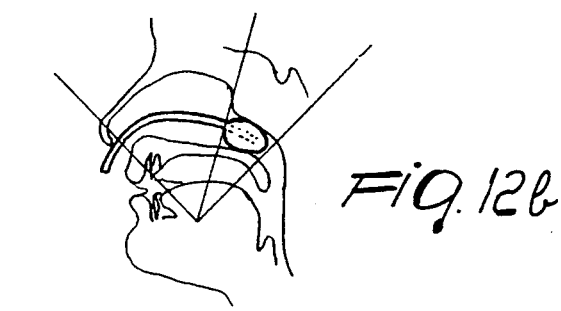

With particular reference to the above figures, the reference numeral 1 generally designates the nasal and/or rhinopharyngeal tampon according to the present invention. In particular, from FIGS. 9a and 9b, the letter A designates the nasal region and the letter B designates the rhinopharyngeal region: nasal and rhinopharyngeal tampons having slightly different shapes are shown in FIGS. 1a, 1b and 3a, 3b, 5a, 5b and 7a, 7b and 9a, 9b and 11a, 11b, while FIGS. 2a, 2b, 6a, 6b and 10a, 10b show nasal tampons, and FIGS. 4a, 4b, 8a, 8b and 12a, 12b show rhinopharyngeal tampons.

The tampon 1 comprises a slightly curved elongated core 2 made of semirigid material and around which there is a shaped body 3, made of elastic spongy material, which is covered by a thin deformable membrane 4 made of impermeable material: the elongated core 2 can be tubular and provided with a parallel through hollow tubular core 8 to allow breathing (examples shown in FIGS. 5-8).

Advantageously, the membrane 4 is made of a material such as silicone, which can adhere to the intranasal mucous membranes without sticking.

The membrane 4 is also obtainable by surface treatment of said body 3.

The membrane 4 is provided with a stem 5 for connection to an aspiration unit 6 (which can be a simple syringe, as shown in the figures, but can also be of any other kind) which is suitable to make the body assume an insertion or extraction configuration (on the left in FIGS. 1 and 2 and on the right in FIG. 3) having a limited volume. The inflow of air through the stem into the shaped body (on the right in FIGS. 1 and 2 and on the left in FIG. 3) is suitable to make said body resume an active configuration having a high volume at atmospheric pressure.

The shaped body is substantially equal in shape to the cavity which it must tampon and is slightly larger, so that when it resumes its large-volume conditions inside the nasal cavity due to the inflow of air into the membrane, it gently presses against the walls of the cavity, thus stopping the flow of blood. It is to be noted that the pressure against the walls of the cavity is gentle and uniform in order to avoid the occurrence of ischemic phenomena in some regions due to excessive compression.

The various components of the tampon are made of materials suitable for medical use.

The figures schematically illustrate tampons in which the core 2 is tubular and is crossed by holes 7, to allow uniform air inflow throughout the body 3, and the stem for connection to the aspiration unit is constituted by the core itself, which is elongated.

Figure 13A:
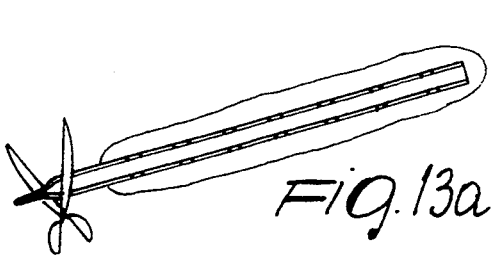
FIGS. 13a and 13b are schematic sectional side views of the tampon according to a further aspect of the invention, in a version ready for use, respectively in an insertion configuration initially under vacuum and in an active configuration at atmospheric pressure after removal of the closed end.
Figure 13B:
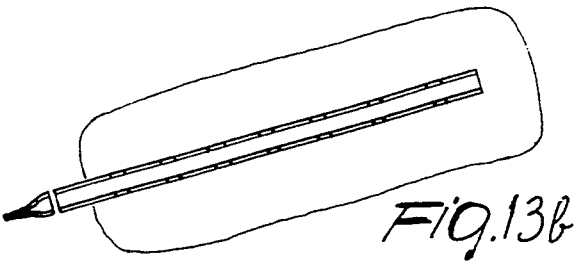

FIG. 13 schematically illustrates a tampon which, when inactive, is subject to a negative pressure and has a stem which, after inserting the deflated tampon into the nasal cavity, is cut in order to allow the expansion of the body 2.

The operation of the tampon according to the invention is as follows: by means of a syringe 6 or the like, the tampon is subjected to negative pressure, so as to assume a configuration having a limited lateral bulk. By virtue of the relative consistency of the core 2 and of its slightly curved shape, the deflated tampon is inserted through the nostrils into the nasal cavity without requiring particular instruments. Once the tampon has been positioned, the syringe is removed (or the stem is cut in the version shown in FIG. 13), and the body 3 made of elastic spongy material tends to return, by inflating with air, to its natural condition of maximum bulk. By means of this return to its natural dimensions, the elastic spongy body applies uniform pressure in all the regions of the nasal cavity, stopping the flow of blood.

When the tampon is removed, in order to facilitate its removal, it is possible to again connect the stem 5 to the syringe and, by aspirating, the body 3 is made to resume its minimum-bulk configuration in order to achieve non-traumatic extraction.

It is to be noted that the patient is allowed to breathe in the embodiments shown in FIGS. 5-8, due to the provision of a further through hollow core 8 for breathing, which is separated from the core 2, and which extends entirely through the body 3.

The tampons shown in FIGS. 9 and 12 can also be effectively applied in paranasal sinuses (maxillary, frontal, ethmoid and sphenoid).

The tampon according to the invention can be associated with any tube which passes through the nasal cavities (for example a nasogastric tube) in order to reach the stomach, the trachea or other parts; by keeping its tip motionless, the possibilities of traumas are limited.

It has thus been observed that the invention achieves the intended objects.

The invention thus conceived is susceptible to numerous modifications and variations, all of which are within the scope of the inventive concept.

All the details may furthermore be replaced with other technically equivalent ones.

In practice, the materials employed, as well as the shapes and dimensions, may be any according to the requirements without thereby abandoning the protective scope of the following claims.

I claim:
1. A nasal tampon comprising:
    a shaped body formed of a mass of elastic spongy material for insertion in a nasal cavity, the shaped body having an outer surface;
    a hollow elongated core element inserted in said mass of elastic spongy material of said shaped body, the hollow elongated core element having an inside;
    at least one hole means provided in said hollow elongated core element for permitting air flow between the mass of elastic spongy material of the shaped body and the inside of said hollow elongated core element;
    a deformable membrane impervious to air which substantially entirely covers the outer surface of said shaped body; and
    a hollow stem element which is inserted through said deformable membrane and which is connected to said hollow elongated core element, said hollow stem element defining an air passage for air flow between the inside of said hollow elongated core element and an environment outside of the deformable membrane;
    said deformable membrane defining an air chamber in which said mass of elastic spongy material is accommodated and which communicates with the environment outside of the deformable membrane by means of said hollow stem element, and said hollow stem element being connectable to an aspirator device for subjecting said air chamber to vacuum thereby to elastically compact said mass of elastic spongy material for effective insertion and removal of said shaped body respectively into and from the nasal cavity.

2. Tampon according to claim 1, wherein said membrane is made of silicone.

3. Tampon according to claim 1, wherein said hollow elongated core element is slightly curved.

4. Tampon according to claim 1, further comprising a breathing hollow core which extends completely through said mass of elastic spongy material of said shaped body, said breathing hollow core having two open ends which extend outside of said deformable membrane, thereby said breathing hollow core defining a passage for breathing of a user.

5. Tampon according to claim 1, further comprising a breathing hollow core which extends completely through said mass of elastic spongy material of said shaped body, said breathing hollow core having two open ends which extend outside of said deformable membrane, thereby said breathing hollow core defining a passage for breathing of a user, said breathing hollow core being arranged parallel to said hollow elongated core element.

* * * * *